(12) United States Patent
Le Blanc

(10) Patent No.: US 7,009,174 B2
(45) Date of Patent: Mar. 7, 2006

(54) DYNAMIC BACKGROUND SIGNAL EXCLUSION IN CHROMATOGRAPHY/MASS SPECTROMETRY DATA-DEPENDENT, DATA ACQUISITION

(75) Inventor: Yves Le Blanc, Toronto (CA)

(73) Assignee: MDS Inc., Concord (CA)

( * ) Notice: Subject to any disclaimer, the term of this patent is extended or adjusted under 35 U.S.C. 154(b) by 118 days.

(21) Appl. No.: 10/819,954

(22) Filed: Apr. 8, 2004

(65) Prior Publication Data

US 2004/0251409 A1    Dec. 16, 2004

Related U.S. Application Data

(60) Provisional application No. 60/461,126, filed on Apr. 9, 2003.

(51) Int. Cl.
*H01J 49/00* (2006.01)
*B01D 59/44* (2006.01)

(52) U.S. Cl. .................. 250/281; 250/282; 250/288
(58) Field of Classification Search .................... None
See application file for complete search history.

(56) References Cited

U.S. PATENT DOCUMENTS

| 2002/0009394 | A1 | 1/2002 | Koster et al. | |
| 2004/0181351 | A1* | 9/2004 | Thompson et al. | 702/76 |
| 2005/0001163 | A1* | 1/2005 | Belov et al. | 250/290 |

OTHER PUBLICATIONS

Covey, T.R. et al., "High-Speed Liquid Chromatography/Tandem Mass Spectrometry for the Determination of Drugs in Biological Samples", Anal. Chem, 58(12):2453-2460, Oct. 1986.

Yu, X et al., "A Novel LC/MS Background Subtraction Technique for the Detection of Drug Metabolites in Biological Samples . . . " Merck Research Labs., West Point, PA 19486.

Windig, W. et al., "A Noise and Background Reduction Method for Component Detection in Liquid Chromatography/Mass Spectrometry", Anal. Chem., 68 (20):3602-3606, Oct. 1996.

* cited by examiner

*Primary Examiner*—Nikita Wells
(74) *Attorney, Agent, or Firm*—Torys LLP

(57) ABSTRACT

A method and system for obtaining mass spectrographic data of a substance. The method includes (a) subjecting the substance to a chromatographic process and ionizing the output thereof; (b) obtaining a current mass spectrogram of the output; (c) identifying at least one ion having a fast rising mass signal by comparing the current mass spectrum obtained In step (b) against one or more previously acquired mass spectrums of the output; and (d) fragmenting the identified ion and recording a mass spectrum resulting therefrom. A mass spectrometer system, includes a chromatography column; a mass spectrometer, including an ion source for ionizing the output of the chromatographic column, in which the mass spectrometer is capable of isolating, fragmenting and mass analyzing an ion of selected mass; and a data-dependent, data acquisition controller programmed to operate the mass spectrometer so as to obtain a current mass spectrogram of the output, identify one or more ions having fast rising mass signals by comparing the current mass spectrum against one or more previously acquired mass spectra of the output, and fragmenting of said identified ions and recording a mass spectrum resulting therefrom.

20 Claims, 7 Drawing Sheets

DYNAMIC BACKGROUND SIGNAL EXCLUSION IN CHROMATOGRAPHY/MASS SPECTROMETRY DATA-DEPENDENT, DATA ACQUISITION

CROSS-REFERENCE TO A RELATED SPECIFICATION

This application claims priority from U.S. Provisional Patent Application No. 60/461,126 filed Apr. 9, 2003.

FIELD OF INVENTION

The invention generally relates to the field of mass spectrometers and more particularly to automatic MS/MS acquisition using data dependent acquisition techniques for identifying eluting compounds in a chromatography/mass spectrum system. The invention can also be used for post-acquisition data processing in the identification of a species of interest in a complex mixture.

BACKGROUND OF INVENTION

Mass spectrometers are often coupled with chromatography systems in order to identify and characterize eluting species from a test sample. In such a coupled system, the eluting solvent is ionized and a series of mass spectrograms are obtained of the eluting solvent at specified time intervals, ranging from, for example, 0.01–10 seconds, for subsequent data analysis. As the test sample may contain many species or compounds, it is often desirable to be able to automatically determine or identify species or compounds of interest as they elute and perform MS/MS analysis to characterize them. However, identifying species of interest in complex mixtures in real time can be a challenging task.

A variety of automation tools and data acquisition & analysis software associated with mass spectrometers have been developed to achieve this goal. A well known automation tool is the Information Dependant Acquisition™ (IDA™) system marketed by MDS Sciex Inc. and Applera Corporation. During the data acquisition process this tool identifies a mass peak in a mass spectrogram so as to select a precursor ion. The tools thus directs one or more subsequent stages of mass spectrometry (MS/MS or MS/MS/MS) in which the chosen precursor ion is fragmented. The resulting MS/MS (or higher) spectrum is a composite of all the fragmentation processes that are energetically allowed: precursor ion to fragment ion and fragment ions to other fragment ions. This spectral richness and/or the dissociation pathways elucidated by subsequent MS stages can be quite useful for identifying compounds when searching through spectral databases or MS/MS libraries or providing structural information used in characterizing compounds.

Vendors of other mass spectrometer systems provide similar real time data dependent switching functions. For example, Thermo Finnigan LLC of San Jose, Calif., markets the Data Dependent Experiment™ (DDE) tool and Waters Corporation (Micromass™) markets the Data Directed Analysis (DDA) tool.

The above-mentioned real time data dependent switching functions provide good results in applications such as in-vitro sample analysis or single protein digest analysis where it is possible to a detect a mass peak of interest fairly easy. However, when dealing with a more complex sample set such as a biological fluid, (e.g., urine or plasma extracts) or mixtures of digested proteins (e.g., digested cell lysate), there may be many other major components or species eluting at the same time that will often "shadow" or hide the signal of the analyte or species of interest, which may have weaker signal intensities, thus making it impossible to effectively select the (ionized) species of real interest. In essence, it is often difficult to automatically detect species eluting at a low level of concentration.

In the IDA™ tool, the selection of the mass peak 'chosen' by the system for MS/MS can be improved by relying on a use and inclusion list or by using more specific survey scans such as neutral loss and precursor scans, as known in the art per se. However, these approaches preclude some knowledge of the sample to be analyzed, which is not always the case. Alternatively, a dynamic exclusion process can be activated wherein, once an ion has been selected for dissociation, that ion is ignored over the next few scans such that the ion having the next most significant intensity peak is selected for dissociation. However, this does not solve the problem of weakly concentrated species that elute simultaneously with a number of other major components.

It will be appreciated that the proper selection of precursor ions is an important step in species identification. The proper selection of ions will also ensure that a useful yet minimal amount of information is collected in data dependent acquisition techniques, which can assist in speeding up and simplifying species identification and characterization.

SUMMARY OF INVENTION

Generally speaking, the invention is able to identify weakly concentrated species that elute simultaneously with a number of other major components by identifying ions having a fast rising mass signal. This is preferably carried out by comparing a mass spectrum(s) against a spectrographic background which may compose one or more previously acquired mass spectrums.

According to one aspect of the invention, a method of obtaining mass spectrographic data of a substance is provided. In the method, a substance is subjected to a chromatographic process and the output thereof is ionized. A mass spectrogram is obtained of the current output. The ion (or ions) having the fastest rising mass signal(s) is/are then identified by comparing the current mass spectrum against a spectrographic background which may comprise one or more previously acquired mass spectrums of the output. Then, the identified ion(s) is/are fragmented and a resulting mass spectrum is recorded. These steps are preferably dynamically repeated so that substantially all eluting species from the chromatographic column are identified by mass and fragmented to obtain additional mass spectral information.

The ion(s) having the fastest rising mass signal may be identified by subtracting one, or an average of, previously acquired mass spectrums from the current mass spectrum. Alternatively, the ion(s) having the fastest rising mass signal may be identified by determining a percentage change in the value of each mass signal in the current mass spectrum against its value or average value in one more of the previously acquired mass spectrums of the output.

If desired, the identified ion may be placed on a dynamic exclusion list. This ion will then not be considered as the fastest rising mass signal thereby enabling the identification and selected of the next-fastest rising ion for a secondary mass analysis. If desired, a precursor or neutral loss scan may also be conducted prior to identifying the ion having fastest rising mass signal.

Once the mass spectrographic data has been acquired, the mass spectrum(s) obtained from the fragmentation of the identified ion(s) can be compared against a database of mass spectrums in order to automatically identify an eluting compound or used for compound characterization.

Systems and apparatus for carrying out the foregoing methods and processes are also disclosed.

BRIEF DESCRIPTION OF DRAWINGS

The foregoing and other aspects of the invention will become more apparent from the following description of specific embodiments thereof and the accompanying drawings which illustrate, by way of example only and not intending to be limiting, the principles of the invention. In the drawings.

DETAILED DESCRIPTION OF PREFERRED EMBODIMENTS

Figure 1:
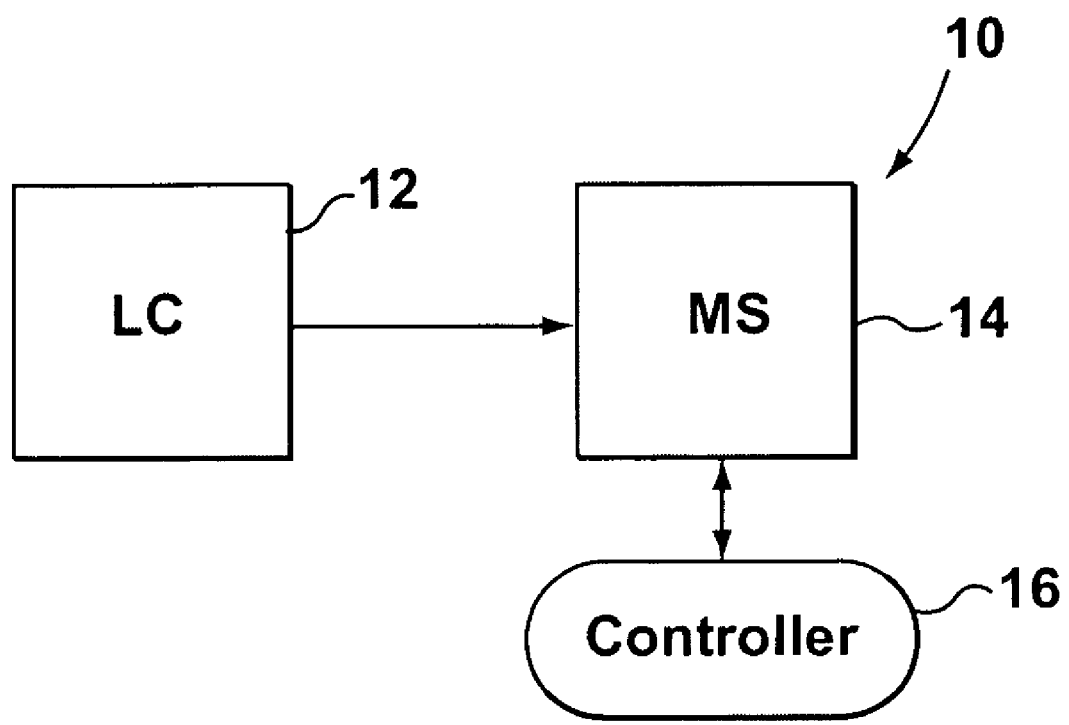
FIG. 1 is a schematic block diagram of an LC/MS system.

FIG. 1 shows the basic components of a liquid chromatography, mass spectrometry (LCMS) system 10 which includes a chromatography column 12 coupled as known in the art per se to a mass spectrometer 14 capable of conducting multiple stages of mass spectrometry, as known in the art per se. An example of such a system is the API 3000™ or API 4000™ LC/MS/MS system marketed by MDS Sciex although those skilled in the art will appreciate that the invention can be applied to any system that has MS and MS/MS capabilities (e.g., a 3D trap). A data-dependent, data acquisition controller 16 enables automated MS to MS/MS acquisition for maximum extraction of information from a single LC/MS run.

Figure 2:
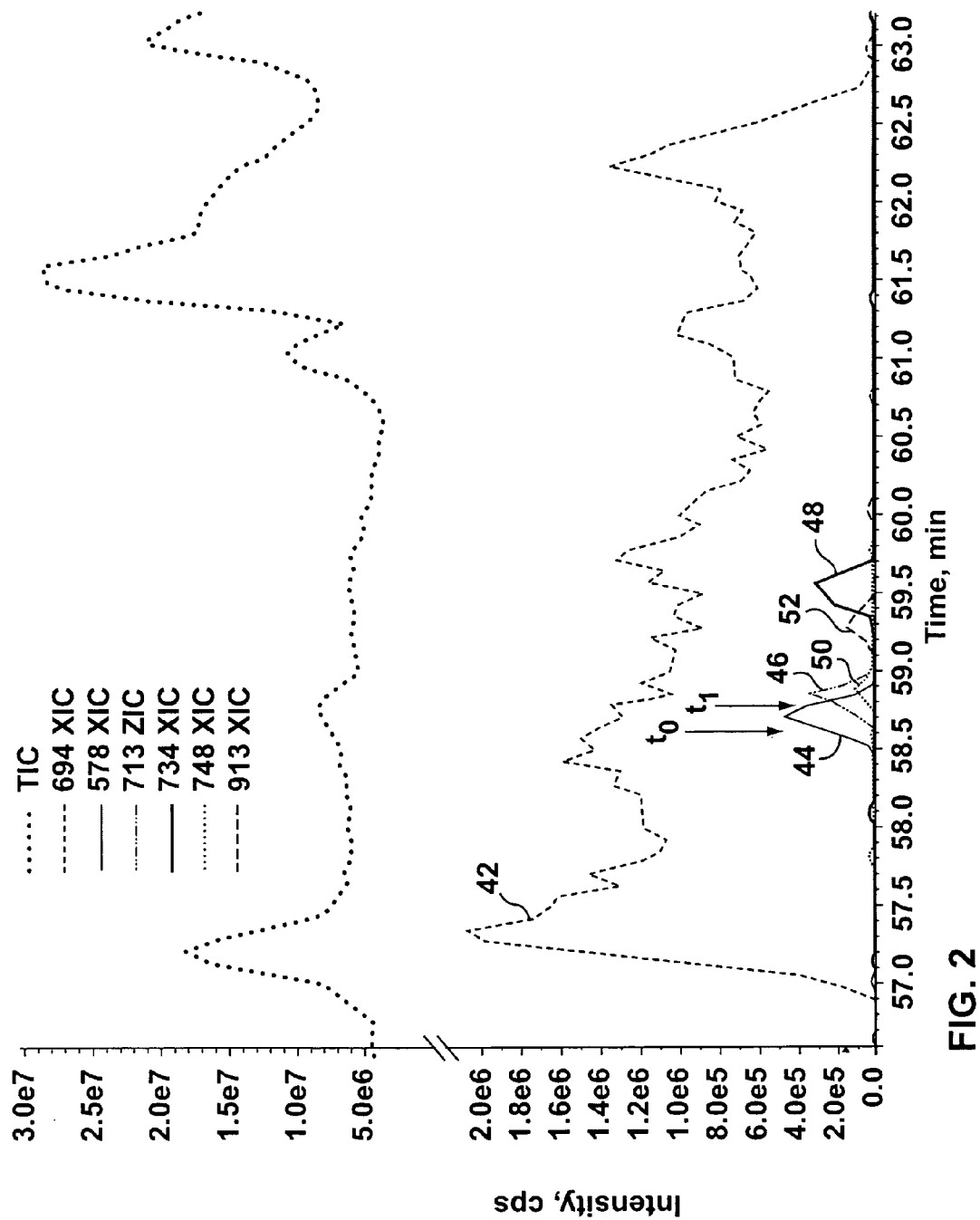
FIG. 2 is a graph which plots the intensity (cps) of various masses detected as function of time (minutes) over a portion of an LC/MS run: TIC (●●●); 694 XIC (- - -) (ref. No 42); 578 XIC (__) (ref. No 44); 713 (_._._..) ref No 46; 734 XIC (__) (ref. No 48); 748 XIC ( . . . ) (ref. No 50); 913 (__) (ref. No 52)

FIG. 2 shows a portion of the data output from an LC/MS run carried out on human growth hormone (Hgh) digest using an API 3000™ system. The data shown pertains to the $57^{th}$ to $63^{rd}$ minutes of the run. Signal 40 plots the total ion intensity (TCI) of the run, which represents the total concentration of all eluting species. The mass spectrometer 14 also records the ion intensity for a predetermined range of masses (more specifically, m/z range) and signals 42 to 52 plot extracted ion counts for ions of mass 694 m/z, 578 m/z, 713 m/z, 734 m/z, 748 m/z and 913 m/z, respectively. These signals chart the intensities of various (but not all) eluting species over this time period.

Figure 3:
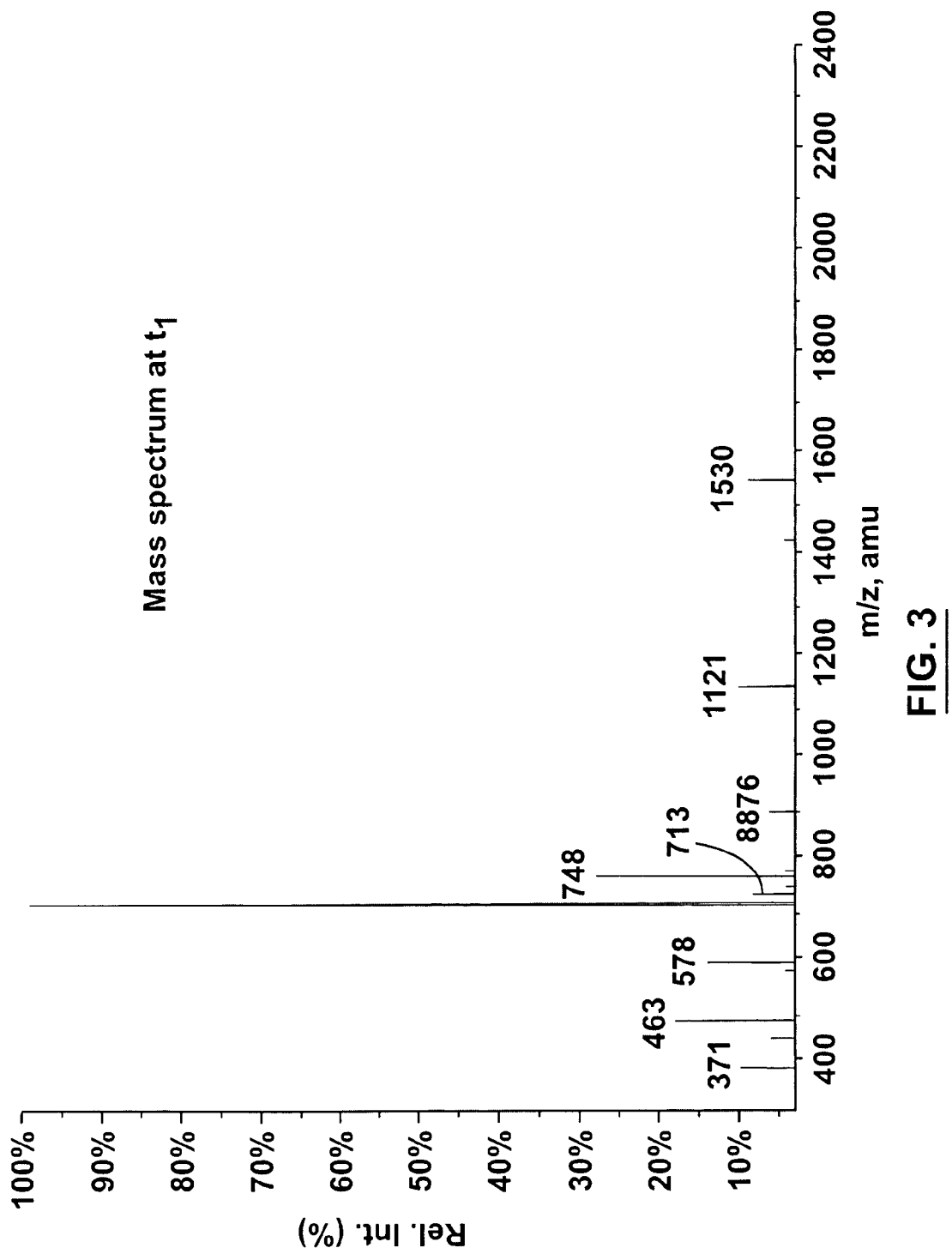
FIG. 3 is a mass spectrogram taken at a first time ($t_1$) in the portion of the LC/MS run shown in FIG. 2.
Figure 4:
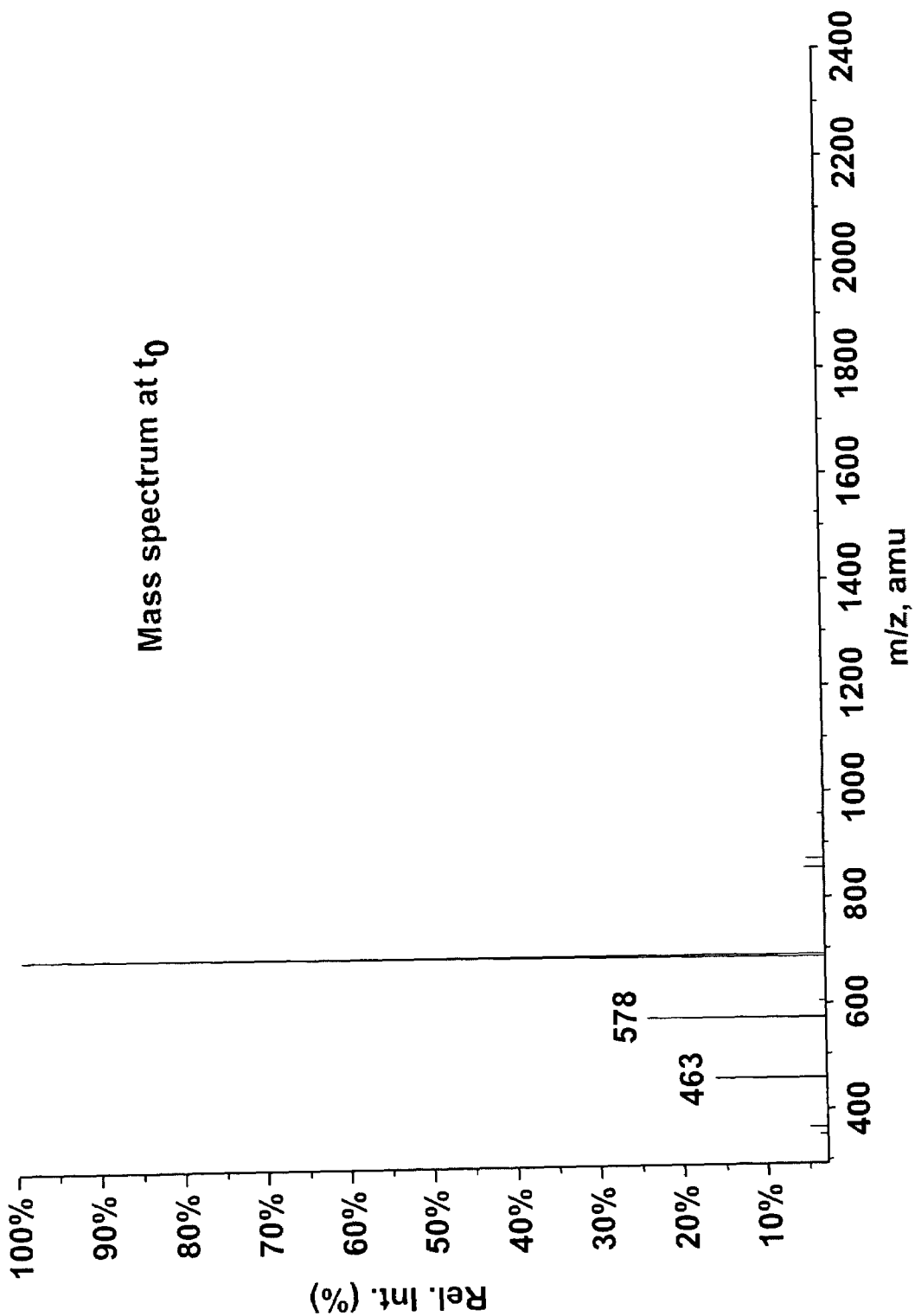
FIG. 4 is a mass spectrogram taken at a second time ($t_0$) in the portion of the LC/MS run shown in FIG. 2.

Note that between approximately 58.5 to 59 minutes of the run, there are a number of eluting species, a subset of which are shown in FIG. 2. The MS spectrograms for these eluting species obtained at times $t_0$ and $t_1$ are shown in FIG. 3 (time $t_1$) and FIG. 4 (time $t_0$), and the ion intensities at each of these instances of time are tabulated in table 1 below.

Figure 5:
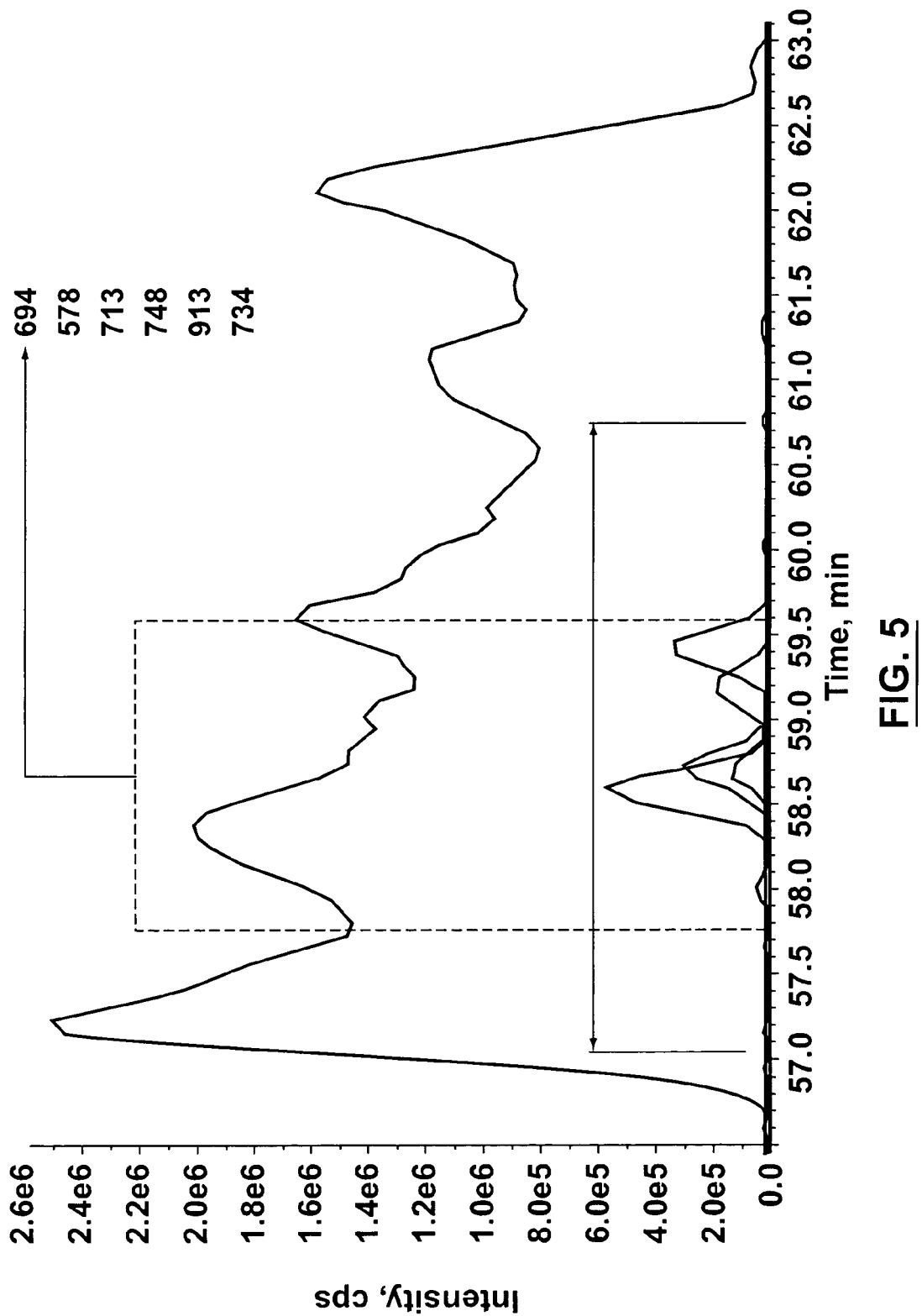
FIG. 5 is a schematic diagram illustrating the ions(s) that would have been selected for a secondary mass analysis using a data-dependent acquisition tool of the prior art without Dynamic Background Signal Exclusion, between 57.16 min—only mass 694 is selected for IDA. However, other masses with chromatographic behavior eluted during that time, representative masses that eluted over the shaded area being listed.

Since a number of mass peaks appear in the spectra at about the same time, the software executed by controller 16 has a difficult time selecting a mass peak on which to conduct a secondary mass analysis. The problem is further exacerbated because a number of low intensity signals (in particular ions of mass 578 m/z, 713 m/z, and 748 m/z) exist in the presence of a high intensity signal generated by ion 694 m/z. FIG. 5 shows that between 57.16 and 60.76 minutes of the run, the prior art data acquisition controller (the IDA™ system) would have selected only ion 694 m/z for conducting a secondary mass analysis (when the system is not programmed to apply dynamic exclusion criterion).

In contrast, the preferred embodiment attempts to identify the fastest rising signal at any given point in time by comparing the most recently acquired MS spectrogram(s) against a dynamic "spectrographic background". For ease of illustration, a simple example of this technique can be understood by comparing FIG. 3 (which is later in time) against FIG. 4 (which is earlier in time). From this comparison it will be seen that mass 748 m/z has the fastest rising signal (which corresponds to signal 50 in FIG. 2).

This phenomenon can be quantified by using two simple quantification methods: (i) a subtraction of the current value of the signal against its value in a previously acquired MS spectrogram; and (ii) a percentage change in the value of the signal. Table 1 shows that by using either of these criterion, ion 748 m/z and 713 m/z will both be moved to the top of the list for the IDA selection.

TABLE 1

| | | | | | IDA Order of Selection | |
| --- | --- | --- | --- | --- | --- | --- |
| m/z | $t_0$ | $t_1$ | Subtraction | Percentage change | Most Intense (prior art) | Background Subt. (preferred embodiment) |
| 578 | 7.33e5 | 7.10e5 | −2.25e4 | −0.03 | 2 | Not selected |
| 694 | 2.95e6 | 2.66e6 | −2.93e5 | −0.10 | 1 | Not selected |
| 713 | 5.00e4 | 1.20e5 | 1.20e5 | 1.40 | 4 | 2 |
| 748 | 5.00e4 | 3.20e5 | 3.20e5 | 5.40 | 3 | 1 |

Having thus selected ions of mass 748 m/z and 713 m/z, the controller 16 can then dynamically operate the spectrometer as known in the art per se to carry out a secondary mass analysis by fragmenting these ions and recording the resulting mass spectrum. In the preferred embodiment, a predetermined number of selected ions are fragmented but in alternative embodiments only the "best" match, e.g., ion 748 m/z, may be selected for subsequent fragmentation.

Both quantification methods described above offer advantages: the percentage or relative gain is the preferred technique when the focus is on rate of growth, whereas the absolute gain calculated by the subtraction method concentrates on species that have a significant increase. The term "fast rising signal" is specifically defined to include a signal rising quickly in relative terms, i.e., calculated by the rate of growth, or in absolute terms, i.e, calculated by the subtraction method.

Figure 6:
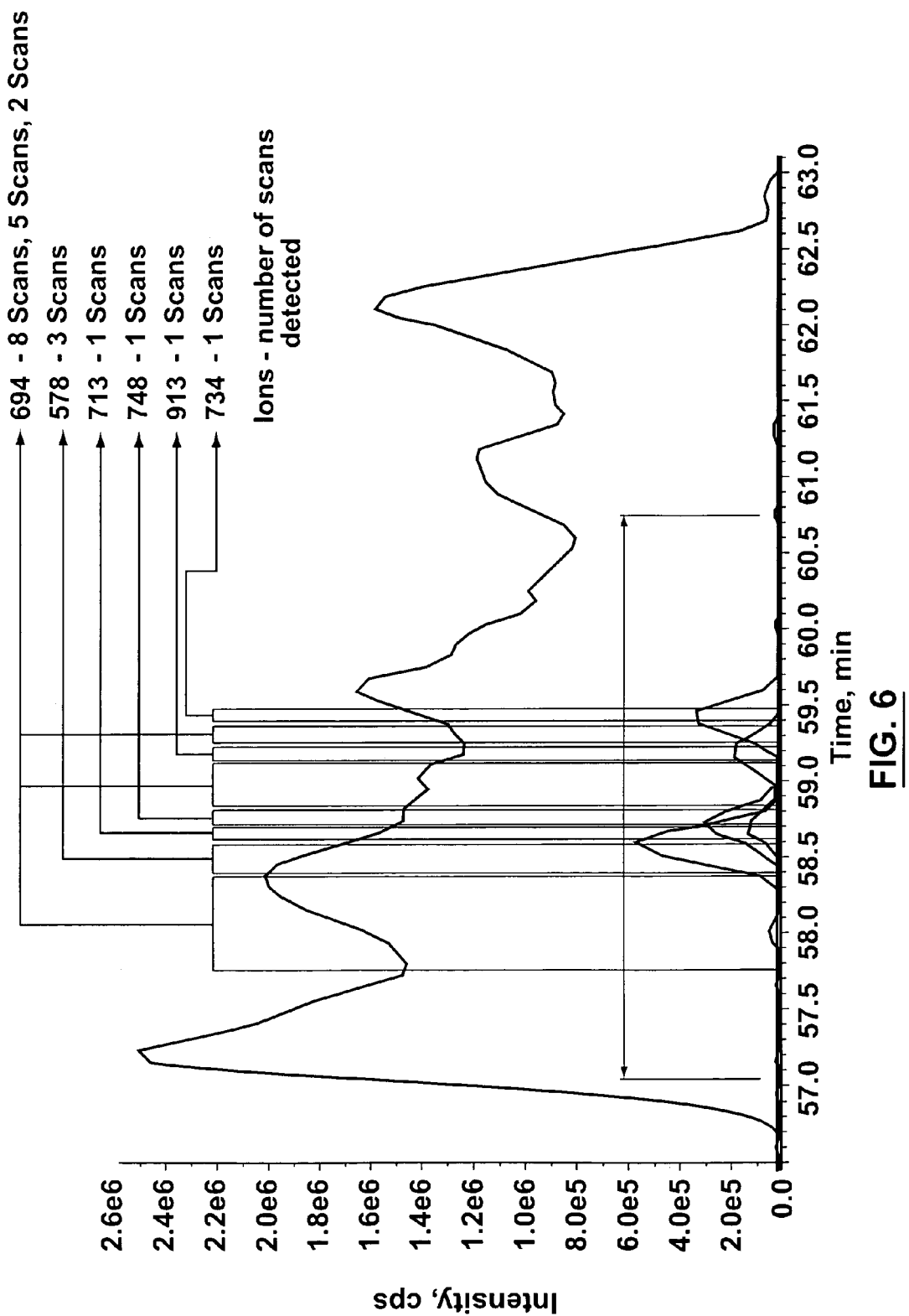
FIG. 6 is a schematic diagram illustrating the ions that are selected for a secondary mass analysis under the preferred embodiment which attempts to identify the fastest rising mass signal at any given point in time. With Dynamic Background Signal Exclusion, more ions were successfully selected for IDA. Even when they were not the base peak of the mass spectrum. If they have a signal rising faster than any other ion, they are detected.

FIG. 6 illustrates the results of these techniques on data obtained between the $57.16^{th}$ and $60.76^{th}$ minutes of the run. Each block 60 represents one or more sequential scans where a different ion mass peak is selected by the controller 16 for conducting a secondary MS analysis.

Figure 7:
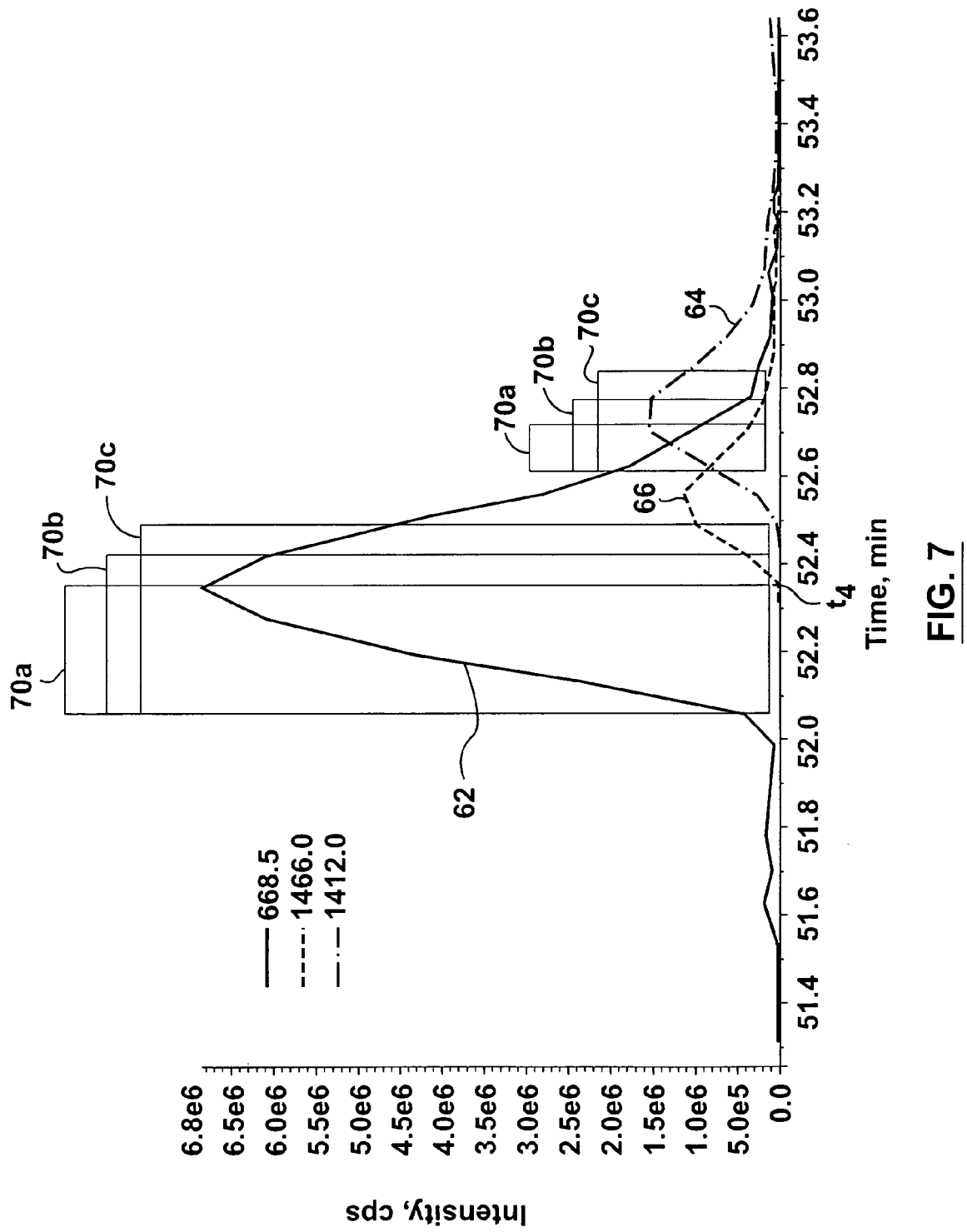
FIG. 7 is a schematic diagram illustrating the proportion of a mass peak which may be considered in the detection of the fastest rising mass signal. With Dynamic Background Signal Exclusion the number of spectra used to determine the average background will determine the number of points that will be selected across an LC peak.

The example presented thus far employed one immediately preceding MS spectrogram to determine the spectrographic background. However, it is possible in the alternative to average a mass signal over a number of MS spectrograms in order to obtain the spectrographic background for comparison purposes. For example, FIG. 7 shows various extracted ion counts obtained during minutes 51.4 to 53.6 of the LC/MS run for ions of mass 668.5 m/z, 1412.0 m/z and 1466.0 m/z, as respectively shown by signals 62, 64 and 66. As indicated by the blocks 70a, 70b, and 70c in FIG. 7, the number of spectra used to determine the average background value of a signal determines the scope of coverage or the number of data points that will be selected across a mass peak. For example, in block 70a the background average value for signal 62 at time $_4$ is obtained from one immediately preceding spectrogram (obtained 5 seconds prior) and hence the controller considers only the rise in the signal. As soon as the signal passes its peak value, the result is a negative number using either a subtraction or percentage change basis, as will be noted by subtracting the value of signal 62 at time $t_4$ from its value at time $t_3$.

However, in block 70b three immediately preceding spectra are used to determine the background value of signal 62, resulting in a greater scope of coverage or number of data points considered across a mass peak. Block 70c indicates the scope of coverage when ten preceding spectra are employed to determine the background value of the signal 62. These techniques, similar to moving averages, assist in smoothing out sudden perturbations in the signals and hence spurious results. The number of spectra the controller uses to determine the average background value of a mass signal is preferably a user-editable parameter.

In the preferred embodiment the selection of an ion for secondary MS analysis may be based on other criterion in addition to or in combination with the criterion of a fastest rising mass signal. For example, if desired, the dynamic background comparison described above may be combined with dynamic exclusion. In this scheme, once an ion has been identified as having the fastest rising mass signal, that ion is placed on an exclusion list and not considered for a predetermined number of subsequent MS scans. This technique can be further augmented by delaying the placement of an ion on the exclusion list until after that ion has been selected a pre-determined number of consecutive times as the ion having the fastest rising mass signal. In addition, if desired, the controller may employ precursor and neutral loss scans prior to the application of the dynamic background comparison.

The invention improves the detection of low intensity species co-eluting in the presence of more concentrated species. Consequently, it is expected that isotope and isotope ratio integrity may be preserved. In addition, the invention offers the possibility of simplifying the number of criteria that a user needs to enter in order to program the controller.

The invention also improves the efficiency in collection of useful information while minimizing the quantity of data collected. This offers the added benefit of minimizing the amount of information that has to be sifted through.

The preferred embodiment has been described with reference to a scan which monitors a single reaction. It will be understood that the invention can be applied to selected ion monitoring (SIM), selected reaction monitoring (SRM), multiple reaction monitoring (MRM) (including where multiple generations of ion transformations are monitored) and multiple charged scans, as known in the art per se. It will also be understood that the invention can be applied to capillary electrophoresis mass spectography systems (CE-MS) and gas chromatography mass spectography systems (GC-MS). Those skilled in the art will appreciate that a variety of modifications may be made to the preferred embodiments without departing from the spirit of the invention.

The invention claimed is:

1. A method of obtaining mass spectrographic data of a substance, comprising:
    a) subjecting the substance to a chromatographic process and ionizing the output thereof;
    b) obtaining a current mass spectrogram of said output;
    c) identifying at least one ion having a fast rising mass signal by comparing the current mass spectrum obtained in step (b) against one or more previously acquired mass spectrums of said output; and
    d) fragmenting said identified ion and recording a mass spectrum resulting therefrom.

2. A method according to claim 1, including repeating steps 1(b) to 1(d) for different portions of said output.

3. A method according to claim 2, wherein ions having fast rising mass signals are identified by subtracting one of said previously acquired mass spectrums from said current mass spectrum.

4. A method according to claim 2, wherein ions having fast rising mass signals are identified by subtracting an average of a plurality of said previously acquired mass spectrums from said current mass spectrum.

5. A method according to claim 2, wherein ions having fast rising mass signals are identified by determining a percentage change in the value of each mass signal in said current mass spectrum against the value of the signal in one of said previously acquired mass spectrums.

6. A method according to claim 2, wherein ions having fast rising mass signals are identified by determining a percentage change in the value of each mass signal in said current mass spectrum against the average value of the signal in a plurality of said previously acquired mass spectrums.

7. A method according to claim 2, including placing at least one identified ion on a dynamic exclusion list thereby to enable the identification of other, fast rising ion(s).

8. A method according to claim 2, including conducting a precursor scan prior to carrying out steps 1(b) to 1(d).

9. A method according to claim 2, including conducting a neutral loss scan prior to carrying out steps 1(b) to 1(d).

10. A method according to claim 2, including comparing the mass spectrum obtained from the fragmentation an identified ion against a database of mass spectrums in order to automatically identify an eluting compound.

11. A mass spectrometer system, comprising:
    a) a chromatography column;
    b) a mass spectrometer, including an ion source for ionizing the output of the chromatographic column, the mass spectrometer being capable of isolating, fragmenting and mass analyzing an ion of selected mass; and c) a data-dependent, data acquisition controller programmed to operate the mass spectrometer so as to:
 i) obtain a current mass spectrogram of said output,
 ii) identify one or more ions having fast rising mass signals by comparing the current mass spectrum against one or more previously acquired mass spectra of said output, and
 iii) fragmenting of said identified ions and recording a mass spectrum resulting therefrom.

12. A system according to claim 11, wherein, for different portions of said output, said controller repeatedly obtains a current mass spectrogram of said output, identifies one or more ions having fast rising mass signals by comparing the current mass spectrum against one or more previously acquired mass spectrums of said output, fragments said identified ion(s) and records a mass spectrum resulting therefrom.

13. A system according to claim 11, wherein ions having fast rising mass signals are identified by subtracting one of said previously acquired mass spectrums from said current mass spectrum.

14. A system according to claim 11, wherein ions having fast rising mass signals are identified by subtracting an average of a plurality of said previously acquired mass spectrums from said current mass spectrum.

15. A system according to claim 11, wherein ions having fast rising mass signals are identified by determining a percentage change in the value of each mass signal in said current mass spectrum against its value in one of said previously acquired mass spectrums.

16. A system according to claim 11, wherein ions having fast rising mass signals are identified by determining a percentage change in the value of each mass signal in said current mass spectrum against its average value in a plurality of said previously acquired mass spectrums.

17. A system according to claim 11, including placing an identified ion on a dynamic exclusion list thereby to enable the identification of other fast rising ions.

18. A system according to claim 11, including conducting a precursor scan prior to identifying fast rising mass signals.

19. A system according to claim 11, including conducting a neutral loss scan prior to identifying fast rising mass signals.

20. A system according to claim 11, including means for comparing the mass spectrum obtained from the fragmentation of an identified ion against a database of mass spectrums in order to automatically identify an eluting compound.

* * * * *